United States Patent
Blanck et al.

(10) Patent No.: US 8,551,713 B1
(45) Date of Patent: Oct. 8, 2013

(54) METHOD FOR QUANTITATIVE ASSESSMENT OF THYMUS INTEGRITY

(75) Inventors: George Blanck, Tampa, FL (US); Mark Lloyd, Tampa, FL (US)

(73) Assignees: University of South Florida, Tampa, FL (US); H. Lee Moffitt Cancer Center and Research Institute, Inc., Tampa, FL (US)

( * ) Notice: Subject to any disclaimer, the term of this patent is extended or adjusted under 35 U.S.C. 154(b) by 32 days.

(21) Appl. No.: 13/295,684

(22) Filed: Nov. 14, 2011

Related U.S. Application Data (60) Provisional application No. 61/413,150, filed on Nov. 12, 2010.

(51) Int. Cl.
*G01N 33/53* (2006.01)

(52) U.S. Cl.
USPC .......................................... 435/7.1; 435/7.2

(58) Field of Classification Search
None
See application file for complete search history.

(56) References Cited

U.S. PATENT DOCUMENTS

| | | |
|---|---|---|
| 2003/0040660 A1 | 2/2003 | Jackowski et al. |
| 2006/0051814 A1 | 3/2006 | Jackowski et al. |
| 2011/0008904 A1 | 1/2011 | Puschett |

OTHER PUBLICATIONS

Coppola D., Parikh V., Boulware D. and Blanck G. (2009) Substantially reduced expression of PIAS1 is associated with colon cancer development. J.Cancer Res.Clin.Oncol. 135, 1287-1291.

Morganti-Kossmann M.C., Satgunaseelan L., Bye N. and Kossmann T. (2007) Modulation of immune response by head injury. Injury, Int. J. Care Injured 38, 1392-1400.

Cualing H.D., Zhong E. and Moscinski L. (2007) "Virtual flow cytometry" of immunostained lymphocytes on microscopic tissue slides: iHCFlow(TM) tissue cytometry. Cytometry B Clin.Cytom. 72B, 63-76.

Paterson D.S., Trachtenberg F.L., Thompson E.G., Belliveau R.A., Beggs A.H., Darnall R., Chadwick A.E., Krous H.F. and Kinney H.C. (2006) Multiple serotonergic brainstem abnormalities in sudden infant death syndrome. JAMA 296, No. 17, 2124-2132.

Leonardo C.C., Hall A.A., Collier L.A., Green S.M., Willing A.E. and Pennypacker K.R. (2010) Administration of a Sigma Receptor Agonist Delays MCAO-Induced Neurodegeneration and White Matter Injury. Transl. Stroke Res. 1, 135-145.

Penit C. and Vasseur F. (1988) Sequential events in thymocyte differentiation and thymus regeneration revealed by a combination of bromodeoxyuridine DNA labeling and antimitotic drug treatment. J.Immunol.140, No. 10, 3315-3323.

Zohar O., Schreiber S., Getslev V., Schwartz J.P., Mullins P.G. and Pick C.G. (2003) Closed-head minimal traumatic brain injury produces long-term cognitive deficits in mice. Neuroscience 118, 949-955.

Levite M. (2008) Neurotransmitters activate T-cells and elicit crucial functions via neurotransmitter receptors. Curr. Opin. Pharmacol. 8, 460-471.

Mocchegiani et al., (1995) Thyroid and thymic endocrine function and survival in severely traumatized patients with or without head injury, Intensive Care Med. 21, 334-341.

*Primary Examiner* — Jacob Cheu (74) *Attorney, Agent, or Firm* — Michele L. Lawson; Smith & Hopen, P.A.

(57) ABSTRACT

The present invention relates to a series of markers and a method of determining cause of death post-mortem by quantifying thymus integrity. An examination of thymuses from human infants suffering mortal head trauma revealed a disruption of the cortical-medullary organization of the thymus, particularly involving dissolution of the cortical-medullary border. A similar result was obtained for related mouse and rat models. The human thymuses from head trauma cases also displayed a higher percentage of Ki67-positive thymocytes.

3 Claims, 11 Drawing Sheets

Fig. 1C.

Suffocation

SIDS

Fig. 4.

Sham treated (4x)

Sham treated (20x)

Stroke (4x)

Stroke (20x)

METHOD FOR QUANTITATIVE ASSESSMENT OF THYMUS INTEGRITY

CROSS REFERENCE TO RELATED APPLICATIONS

This application claims priority to U.S. Provisional Application No. 61/413,150 entitled "A Method for Quantitative Assessment of Thymus Integrity", filed Nov. 12, 2010, the contents of which are hereby incorporated by reference into this disclosure.

FIELD OF INVENTION

This invention relates to methods of quantitative assessment of thymus integrity. Specifically, the invention develops a series of markers and a method of determining the manner of death in a child or infant by assessing the integrity of the thymus post-mortem.

BACKGROUND OF THE INVENTION

Functional links have been found between the brain, endocrine and immune system as referenced in Mocchegiani et al. (Thyroid and thymic endocrine function and survival in severely traumatized patients with or without head injury, *Intensive Care Med,* 1995, 21:334-341), incorporated herein in its entirety by reference. The general consensus is that there is a presence of strongly reduced thyroid hormone serum levels in head trauma. Further, following severe head trauma, specific immunity, particularly T-cell mediated immunity is found to be altered in that there is a decreased ratio of T-helper/T-suppressor cells, reduced mitogen responsiveness and impaired cutaneous delayed hypersensitivity.

Mocchegiani et al. suggested involvement of the thymic function in the depressed immunity of patients having head trauma. They determined the blood concentration of thymulin in head trauma injured patients and compared this result with that found in patients without head trauma. These values were correlated with thyroid hormone concentrations and the impact that the thymic hormone measurements have for predicting overall survival of the patient. Blood samples were taken from the patients within 24 hours after admission and then again 5 and 10 days later. Mocchegiani found that thymic endocrine activity as measured by the level of thymulin, a thymic peptide, is reduced in those patients having a head injury as compared to patients without a head injury. Mocchegiani also found that this reduction of thymic endocrine activity is correlated with the depth of coma, i.e. the clinical indication of the severity of brain damage. Mocchegiani postulates that the low thymulin levels of the patients suffering from head injury may be due to a reduced production of this peptide by the thymus. All of the studies of Mocchegiani involved adults having head injury.

Traumatic brain injury (TBI) is broadly defined as damage to the brain as a result of physical force which may cause alteration of normal brain processes due to changes in the brain structure or function. A closed head traumatic brain injury can be caused by a rapid movement of the head which causes the brain to essentially bounce off the inside of the skull. A closed head TBI may be the result of a motor vehicle accident, a fall, or forceful shaking as in Shaken Baby Syndrome. Shaken Baby Syndrome is defined as one or more of a group of symptoms (as limb paralysis, epilepsy, vision loss, or mental retardation) that tend to occur in an infant which has been severely shaken but that may also result from other actions (as tossing) causing internal trauma (as hemorrhage, hematoma, or contusions) especially to the brain region, and that may ultimately result in the death of the infant. Determining the cause of death of an infant can be a very difficult task especially as it relates to sudden infant death syndrome (SIDS) or shaken baby syndrome.

As illustrated above, a great deal of work has been devoted to the impact of head trauma and brain function on the immune system, however there has not been an examination of the effect of head trauma on the thymus, the site of maturation and negative selection of T-cells, and the source of circulating T-cells. What is needed is a quantitative assessment of post-mortem thymus integrity. Thymus integrity in children could reflect manner of death. Less integrity is correlated with more traumatic death. Thus, a more universal (quantitative, standardized) process for assessing post-mortem thymus integrity could aid in determining manner of infant or child death.

SUMMARY OF INVENTION

An examination of thymuses from human infants suffering mortal head trauma revealed a disruption of the cortical-medullary organization of the thymus, particularly involving dissolution of the cortical-medullary border. A similar result was obtained for related mouse and rat models. The human thymuses from head trauma cases also displayed a higher percentage of Ki67-positive thymocytes. Finally, in the course of this work, the inventors determined that the human serotonin receptor and the serotonin transporter are expressed almost exclusively in the thymic medulla, as opposed to the thymic cortex.

In an embodiment, a method of quantitatively determining head trauma in a subject suspected of suffering from head trauma is presented comprising: obtaining a thymic tissue sample from the subject; determining the number of Ki67 positive thymocytes in the sample; and comparing the number of Ki67 positive thymocytes in the sample to the number of Ki67 positive thymocytes in a thymic tissue sample taken from a normal subject not suffering from head trauma; wherein an increase in KI67 positive thymocytes in the sample from the subject suspected of suffering from head trauma as compared to the sample from the normal subject is indicative of head trauma. The subject may be a human, including a child.

The number of Ki67 positive thymocytes may be determined by staining the thymus samples with anti-Ki67 and counting the stained thymocytes.

In another embodiment, a method of quantitatively determining head trauma in a subject suspected of suffering from head trauma is presented comprising: obtaining a thymic tissue sample from the subject; and performing analysis on the sample to quantify the amount of interstitial space present between thymocytes; wherein an increase in the interstitial space as compared to the total area of space is indicative of head trauma. The subject may be a human including a child.

The analysis to determine the amount of interstitial space can be further comprised of calculating a ratio of interstitial space over total area of the thymus. A ratio of over about 27% of the total area being comprised of the interstitial space is indicative of head trauma.

In a further embodiment, a method of quantitatively determining head trauma in a subject suspected of suffering from head trauma is presented comprising: obtaining a thymic tissue sample from the subject; obtaining a thymic tissue sample from a normal subject; and performing analysis on the sample from the subject suspected of suffering from head trauma to determine the integrity of the cortical-medullary border; wherein a disruption of the cortical-medullary border of the sample from the subject suspected of suffering from head trauma as compared to the normal sample is indicative of head trauma. The subject can be a human including a child. The analysis can be a line trace.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that there are other embodiments by which the invention may be practiced. It is to be understood that other embodiments may be utilized and structural changes may be made without departing from the scope of the invention.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range, to the tenth of the unit. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

"Subject" is used to describe an animal, preferably a human. "Subject" and "patient" are used interchangeably herein.

The term "sample" as used herein refers to any physical sample that includes a cell or a cell extract from a cell, a tissue, or an organ including a biopsy sample. The sample can be from a biological source such as a subject or animal, or a portion thereof. Samples from a biological source can be from a normal or an abnormal organism, such as an organism known to be suffering from a condition such as head trauma, or any portion thereof. Samples can also be from any fluid, tissue or organ including normal and abnormal (fluid, tissue or organ). Samples from a subject or animal can be used in the present invention as obtained by the subject or animal.

The term "about" as used herein is not intended to limit the scope of the invention but instead encompass the specified material, parameter or step as well as those that do not materially affect the basic and novel characteristics of the invention.

The term "disruption" as used herein refers to any break in the integrity of the thymus. For example, there may be a complete or partial dissolution of the cortical-medullary border of the thymus or there may be a disorganization of the internal structure of the thymus such as increased interstitial space among the thymocytes.

The term "normal" as used herein refers to a subject that has not undergone head trauma of any sort.

The term "child" as used herein refers to a human under the age of 13 years and preferably under the age of 5 years. The terms "infant" and "child" are used interchangeably herein.

An examination of thymuses from human infants suffering mortal head trauma revealed a disruption of the cortical-medullary organization of the thymus, particularly involving dissolution of the cortical-medullary border. A similar result was obtained for related mouse and rat models. The human thymuses from head trauma cases also displayed a higher percentage of Ki67-positive thymocytes. Finally, in the course of this work, the inventors determined that the human serotonin receptor and the serotonin transporter are expressed almost exclusively in the thymic medulla, as opposed to the thymic cortex.

A great deal of work has recently been directed towards the impact of brain function and head trauma on the immune system (Morganti-Kossmann M. C., Satgunaseelan L., Bye N. and Kossmann T. (2007) Modulation of immune response by head injury. Injury 38, 1392-1400), but very little is known regarding the effect of head trauma on the thymus, the site of maturation and negative selection of T-cells, and the source of circulating T-cells. The inventors examined the thymuses of human infants deceased from brain trauma and observed that these thymuses had disrupted architecture and a significant dissolution of the cortical-medullary border, as compared to infants deceased from suffocation or sudden infant death syndrome (SIDS). Furthermore, head trauma correlated with an increase in Ki67 staining of thymocytes indicating the induction of a proliferative response.

Materials and Methods

Paraffin embedded, formalin fixed tissue was prepared for microscopy as described in Coppola (Coppola D., Parikh V., Boulware D. and Blanck G. (2009) Substantially reduced expression of PIAS1 is associated with colon cancer development. J. Cancer Res. Clin. Oncol. 135, 1287-1291). Sections were stained with hematoxylin and eosin (H & E) and immunohistochemistry was performed with rabbit polyclonal anti-serotonin receptor-1a and anti-SERT. Slides were scanned using the Aperio™ (Vista, Calif.) ScanScope XT with a 20×/0.8NA objective lens at a rate of about 2 minutes per slide via Basler tri-linear-array. Image analysis was performed using a Positive Pixel Count v9.1 algorithm with the following customized thresholds [Hue Value=0.2; Hue Width=0.6; Color Saturation Threshold=0.05; IWP(High) =210; Iwp(Low)=Ip(High)=160; Ip(low)=Isp(High)=80 Isp (Low)=0]. The algorithm was applied to the entire scanned slide image to detect regions of increased interstitial space by detecting pixels that satisfy the color and intensity specification defined above. Data were combined by condition, and the ratio of interstitial space over total area was defined by pixels and plotted as a bar graph in FIGS. 1D, 3.

Figure 2A:
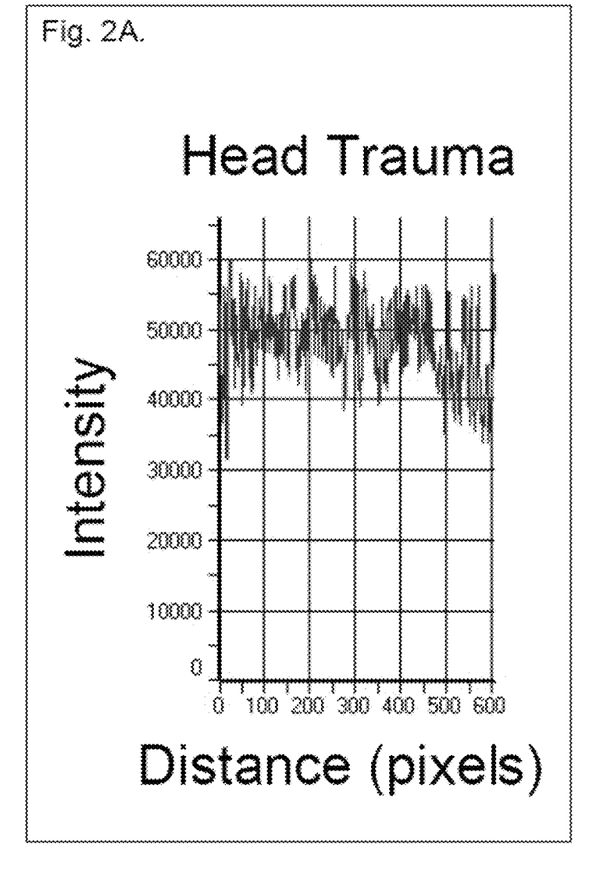
FIG. 2A-C are one dimensional plots indicating the extent of cortical-medullary border integrity in individual lobules of human thymuses due to (A) head trauma; (B) suffocation; and (C) SIDS.
Figure 2B:
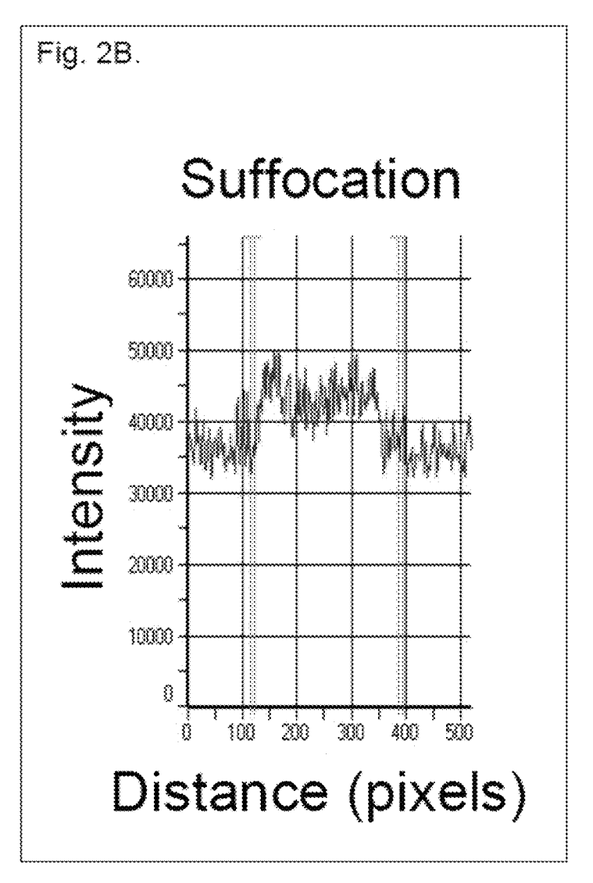
Figure 2C:
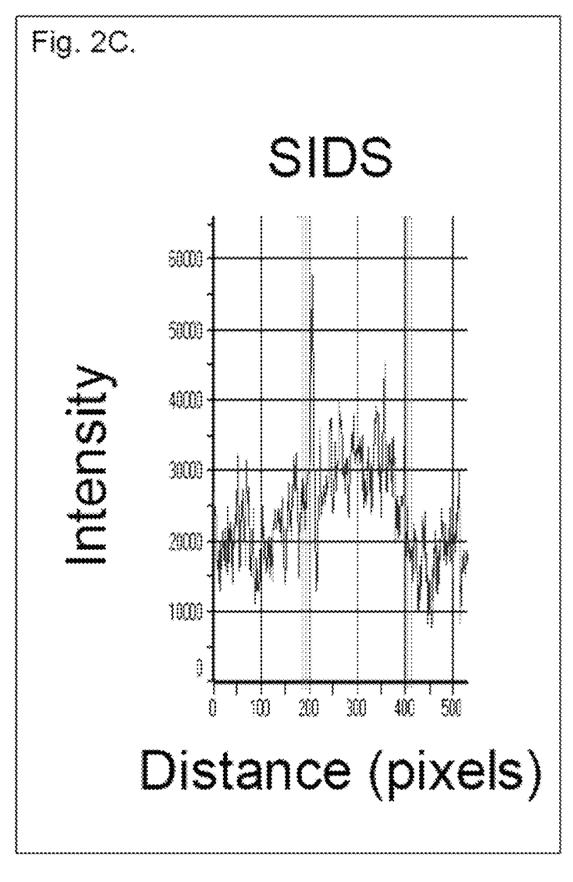

Line profile traces were objectively applied across cortical and medullar border regions at 0°, 45° and 90° to graphically represent border integrity retention across each sample type (FIG. 2) using the raw RGB and grey scale image sets.

The mouse head trauma model uses a dropping weight that delivers a noninvasive, closed-skull injury to the brains of the mice (Zohar O., Schreiber S., Getslev V., Schwartz J. P., Mullins P. G. and Pick C. G. (2003) Closed-head minimal traumatic brain injury produces long-term cognitive deficits in mice. Neuroscience 118, 949-955). Briefly, at the time of injury, mice were lightly anesthetized with isoflurane and placed on a sponge, underneath a metal tube (13 mm diameter×80 cm long), so that the impact to the skull would be immediately anterior to the right ear. The metal weight was dropped down the tube, striking the temporal region of the skull. Permanent Rat Middle Cerebral Artery Occlusion (MCAO) procedures were as described (Leonardo C. C., Hall A. A., Collier L. A., Green S. M., Willing A. E. and Pennypacker K. R. (2010) Administration of a Sigma Receptor Agonist Delays MCAO-Induced Neurodegeneration and White Matter Injury. Transl. Stroke Res. 1, 135-145). Briefly, rats were anesthetized in an induction chamber with 3-4% isoflurane in oxygen. Anesthesia was maintained with 2.5-3% isoflurane in oxygen delivered at 1 liter/minute. The carotid bifurcation was exposed by incising the skin and fascia ventral to the right sternocleidomastoid muscle. The vagus nerve was dissected free of the right common carotid artery before the common carotid artery was clamped. Two 5-0 ligatures, one distal and one proximal, were used to cinch the external carotid artery closed, following which the artery was transected between the ligatures. Branches of the external carotid artery were cauterized as needed to control bleeding. The proximal ligated stump of the external carotid artery was then used as a portal to pass an occluder (fishing line) into the lumen of the internal carotid artery as follows: The proximal stump of the external carotid artery was perforated with a 40 mm length of 6 pound test monofilament which was then introduced into the lumen of the carotid bifurcation and thence into the internal carotid artery. This occluder was fed rostrally through the middle cerebral artery (MCA) until resistance was met (usually at about 25 mm), signaling complete occlusion of the MCA. At this time the occluder was permanently secured, the clamp on the common carotid was removed, and Gelfoam was placed over the carotid fascia. A Laser Doppler Monitor was used to determine reductions in blood flow. Animals that did not show≥60% reduction in blood flow following introduction of the occluder were excluded from the study.

To accurately and efficiently assess Ki-67 expression in immunostained thymus tissue, the VirtualFlow™ technique was used (IHCFLOW Inc, Tampa, Fla.). This software generates a two-parameter dot-plot display, similar to those generated in flow cytometry. The microscopic images were captured using a 20×, 0.4-NA objective (Leica, Westlar, Germany) and a color brightfield CCD high resolution camera (Diagnostic Instruments). Each image is 512×474 pixels, with 1.5 pixels per micron. No manual or interactive labeling or shading or color correction was performed. The light intensity rheostat was set to 7.0 of 12.0. The light source was a 30 watt 12 v incandescent bulb with a condenser blue filter, 80a Tiffen, with the condenser aperture set a 0.5 ph. This method automatically converts digital images of immunostained tissue to percentage positive, using a multi-thresholding, iterative bit slice identification of stained nuclei and unstained nuclei. The single cell count-results correlate with both manual Ki-67 scoring and standardized tissue flow cytometry results (Cualing H. D., Zhong E. and Moscinski L. (2007) "Virtual flow cytometry" of immunostained lymphocytes on microscopic tissue slides: iHCFlow tissue cytometry. Cytometry B Clin. Cytom. 72, 63-76). Briefly, thymic sections previously immunostained as described (Coppola et al. 2009) using Ki-67 AP-DAB (Mib-1, Ventana) by automated Ventana XT (Tucson, Ariz.) are put on the stage. The nuclei (brown stained) and hematoxylin (blue counterstained) image plane is manually focused, captured, and saved as jpeg file. Segmentation and display of histogram and statistical results table takes 3-4 seconds. An average of 40 frames (with 329-811 cells/frame) was captured per slide on all thymic cortex and medulla regions. Results were tabulated and analyzed per region and per subject thymus using ANOVA (Graphpad software).

Results

The inventors obtained a series of thymus samples from human infants deceased from head trauma, SIDS, or suffocation. The original goal was to determine differences in thymus serotonin receptor-1a or SERT expression, between thymuses from infants whose cause of death was given as SIDS compared to those dying from known events of suffocation or head trauma (Paterson D. S., Trachtenberg F. L., Thompson E. G., Belliveau R. A., Beggs A. H., Darnall R., Chadwick A. E., Krous H. F. and Kinney H. C. (2006) Multiple serotonergic brainstem abnormalities in sudden infant death syndrome. JAMA 296, 2124-2132). No such differences were observed.

However, upon analysis of the sample set, two observations were made. First, the expression of both the serotonin receptor-1a and SERT were highly concentrated in the medulla of all samples.

Figure 1A:
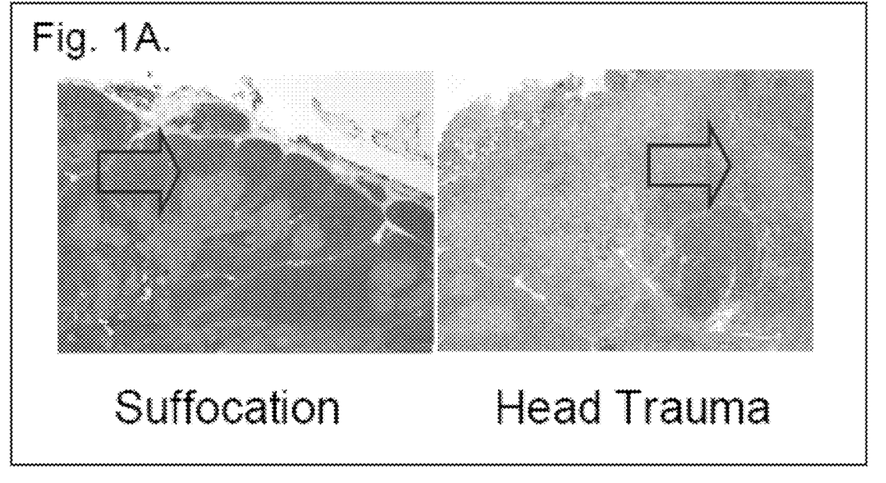
FIG. 1A is an image of H&E stain of human thymuses from infants suffering fatal suffocation or head trauma. Arrowheads indicate intact cortical-medullary architecture and disrupted cortical-medullary architecture, respectively.
Figure 1B:
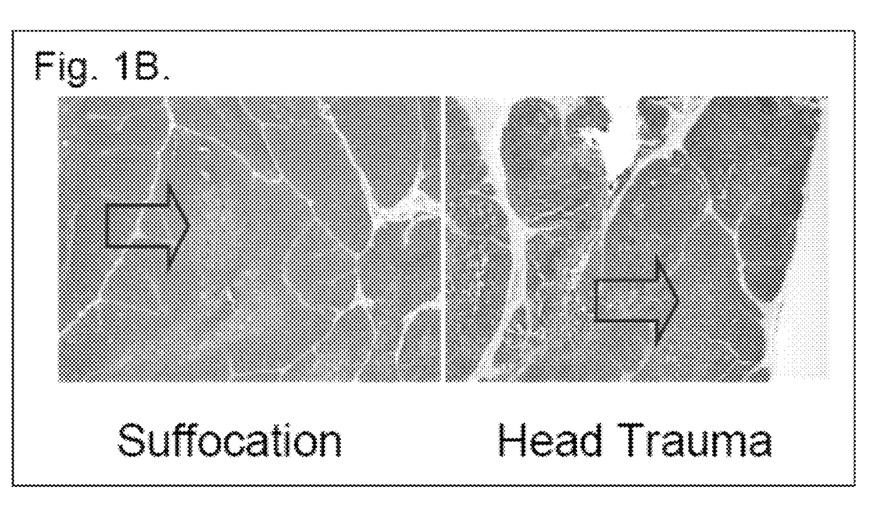
FIG. 1B is an image showing SERT staining of thymuses from infants suffering fatal suffocation or head trauma. Arrowheads indicated largely medullary specific staining or diffuse staining, respectively.
Figure 1C:
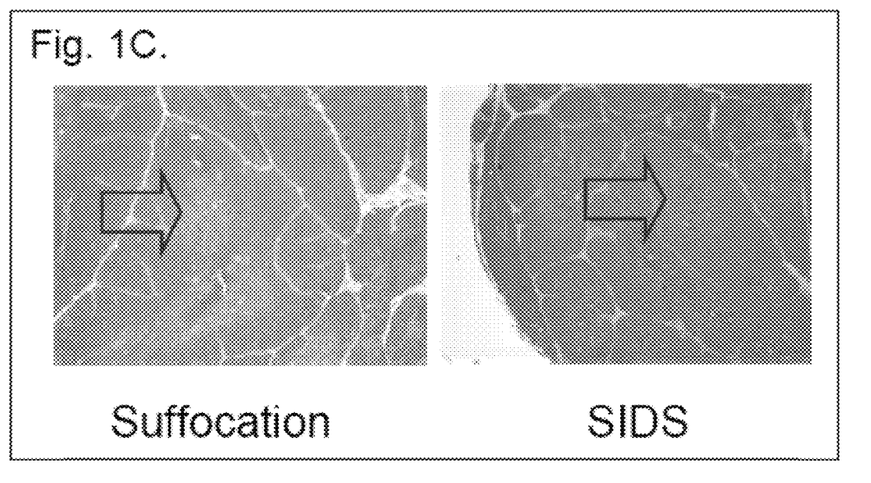
FIG. 1C is an image showing SERT staining of thymuses from infants suffering fatal suffocation or SIDS. Arrowheads indicate largely medullary specific staining.

Second, thymuses from head trauma were highly disorganized, particularly having extensive interstitial space among the thymocytes and a disrupted cortical-medullary border (FIG. 1A-C), the region of entry of pre-T-cells into the thymus (Penit C. and Vasseur F. (1988) Sequential events in thymocyte differentiation and thymus regeneration revealed by a combination of bromodeoxyuridine DNA labeling and antimitotic drug treatment. J. Immunol. 140, 3315-3323). This appearance has been referred to as a "starry sky" or marbled appearance for thymuses representing other pathological situations.

Figure 1D:
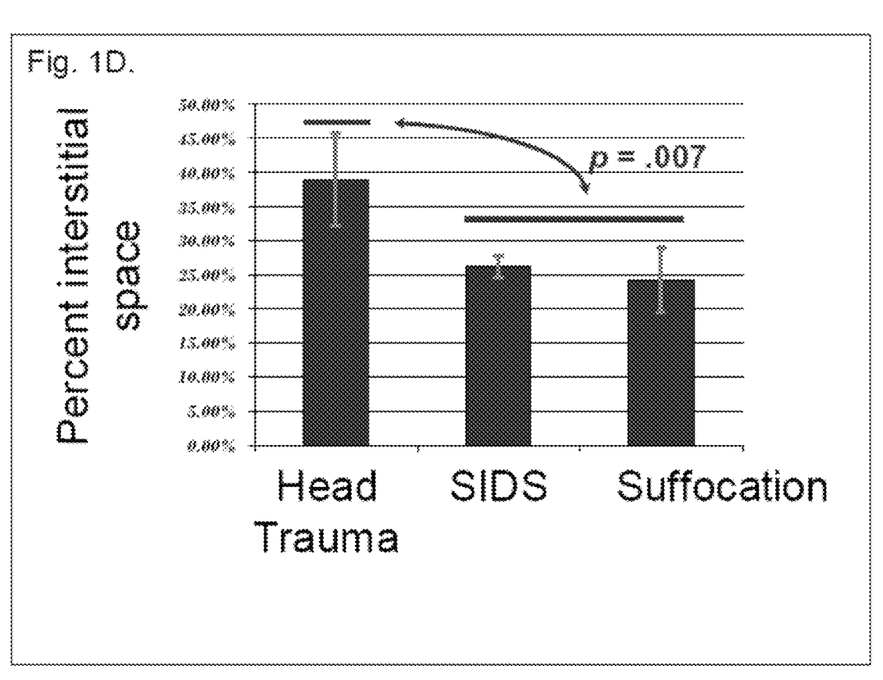
FIG. 1D is a graph illustrating quantification of the interstitial space between thymocytes in human head trauma versus suffocation and SIDS thymuses.

To statistically assess the distinctions between the head trauma thymuses and the suffocation/SIDS thymuses, the interstitial space was quantified as indicated in the above Materials and Methods section, revealing a statistically significant difference (FIG. 1D). Furthermore, disruption of the border could be represented by a line-trace, providing an alternative, quantitative comparison of the border integrity for different samples (FIG. 2.)

Figure 3:
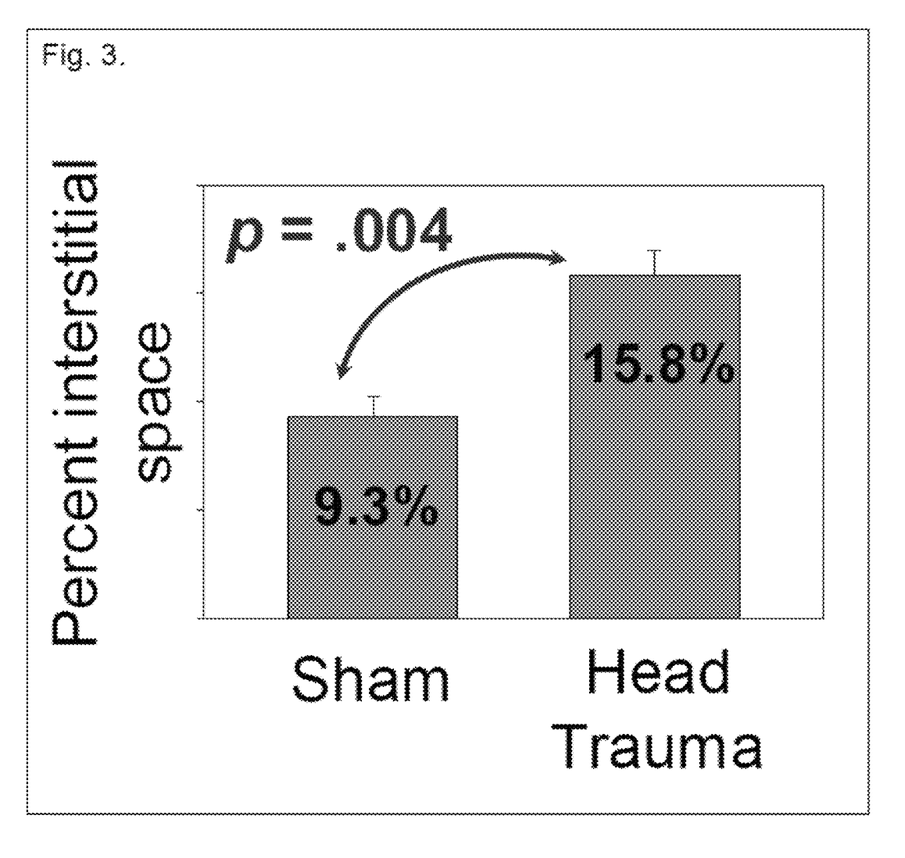
FIG. 3 is a graph illustrating quantification of the interstitial space in mouse thymuses with head trauma versus sham treated animals.
Figure 4:
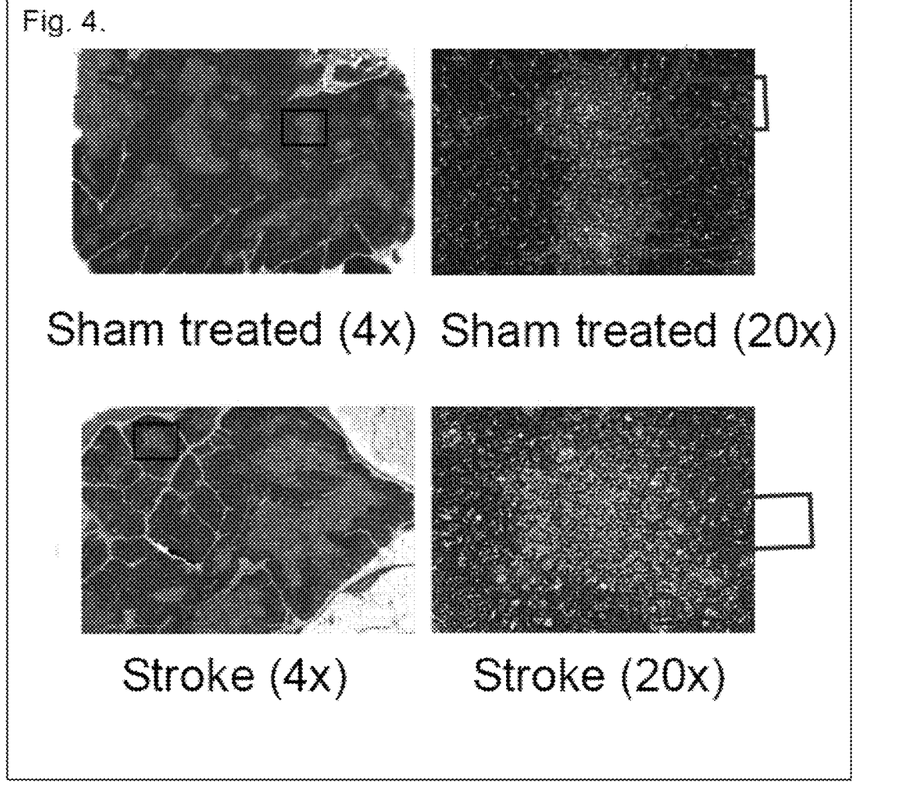
FIG. 4 is a series of images of representative micrographs of the thymus medulla and cortex from a sham treated and rat stroke model. Arrowheads indicate sharp or diffuse cortical-medullary border, respectively.

To support the conclusion that thymus disruption correlated with head trauma, and to establish an animal model for future studies, a mouse head trauma model was employed as described in the Materials and Methods section. Analysis of H & E stained thymus sections showed that thymuses from mice receiving head trauma had a significantly increased level of interstitial space compared to sham-treated mice (FIG. 3). A qualitative assessment of a rat stroke model gave a similar result (FIG. 4).

Figure 5A:
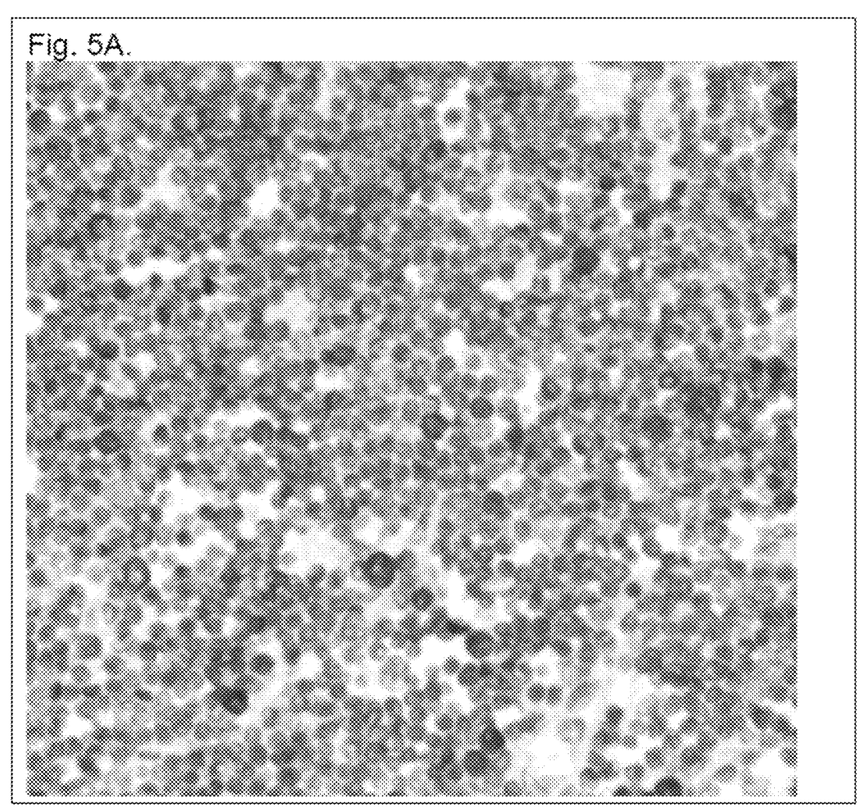
FIG. 5A is an image illustrating an example Ki67 staining of a human thymus.
Figure 5B:
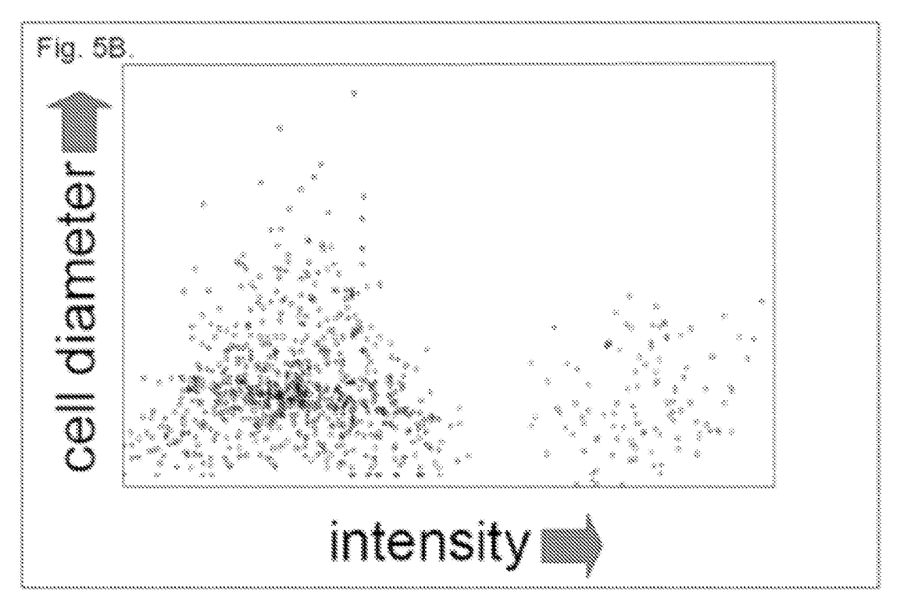
FIG. 5B is a graph depicting the virtual flow results from FIG. 5A.
Figure 5C:
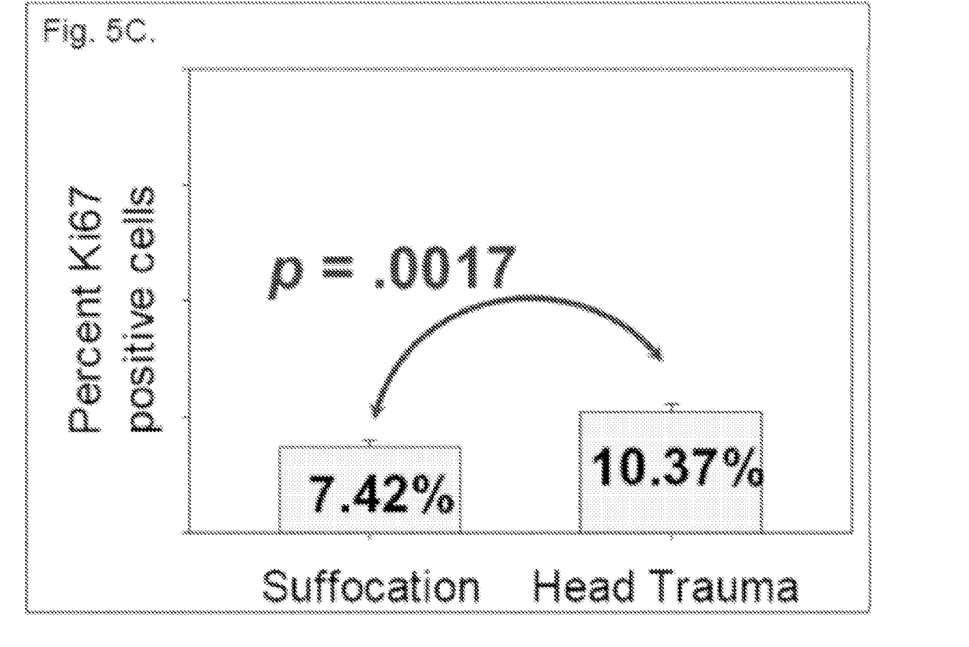
FIG. 5C is a graph illustrating quantification of Ki67 staining in thymuses from human head trauma versus suffocation.

To begin to assess the molecular and cellular changes underlying the disorganization of the thymus associated with head trauma, thymuses were stained with anti-Ki67. An increase in Ki67-positive thymocytes in the thymuses from head trauma victims was found (FIG. 5).

These results indicate that serotonin receptor-1A expression and SERT expression on thymocytes is concentrated in the medulla, where mature T-cells reside. The role of serotonin in T-cell function remains to be elucidated, but in general, reports indicate that serotonin exposure leads to, or facilitates T-cell activation (Levite M. (2008) Neurotransmitters activate T-cells and elicit crucial functions via neurotransmitter receptors. Curr. Opin. Pharmacol. 8, 460-471).

The results described above also indicate that head trauma leads to a disruption of thymus architecture, which can be quantified as increased interstitial space between the thymocytes. The nature of the interstitial space has not been determined, but this space likely includes thymic epithelia cells, macrophage, and edema. Head trauma was also associated with an increase in Ki67 positive thymocytes, representing an increase in thymocytes undergoing DNA replication. Future studies will be oriented towards understanding the mechanism of the effect of head trauma on the thymus and the implications for the effect of head trauma on the immune system. Future studies will be done to determine if on-fatal head trauma reduces apoptosis of self-reactive thymocytes or affects the number of self-reactive thymocytes entering the periphery.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method of quantitatively determining head trauma in a child subject suspected of suffering from head trauma comprising:
   obtaining a thymic tissue sample from the subject;
   obtaining a thymic tissue sample from a normal subject; and
   performing analysis on the sample from the subject suspected of suffering from head trauma to determine the integrity of the cortical-medullary border;
   wherein a disruption of the cortical-medullary border of the sample from the subject suspected of suffering from head trauma as compared to the normal sample is indicative of head trauma wherein the disruption of the cortical-medullary border can be quantified by the increase of the interstitial space between the thymocytes.

2. The method of claim 1, wherein the analysis is a line trace.

3. The method of claim 1, wherein the subject is a human.

* * * * *